United States Patent [19]

Hata et al.

[11] 4,245,048
[45] Jan. 13, 1981

[54] PROCESS FOR PRODUCING COENZYME $Q_{10}$

[75] Inventors: Kunio Hata, Soka; Kihachiro Ohshima, Tokyo; Isao Kano, Tokyo; Motoi Matsui, Tokyo; Tadaaki Sato, Akita, all of Japan

[73] Assignee: Jujo Paper Co., Ltd., Tokyo, Japan

[21] Appl. No.: 77,430

[22] Filed: Sep. 20, 1979

[30] Foreign Application Priority Data

Sep. 25, 1978 [JP] Japan .................................. 53-116732

[51] Int. Cl.[3] .............................................. C12P 7/66
[52] U.S. Cl. ............................... 435/133; 435/251; 435/911
[58] Field of Search ............................... 435/133, 251

[56] References Cited

U.S. PATENT DOCUMENTS

| | | | |
|---|---|---|---|
| 3,933,590 | 1/1976 | Oguma et al. | 435/251 |
| 4,070,244 | 1/1978 | Nakao et al. | 435/133 |

*Primary Examiner*—Alvin E. Tanenholtz
*Attorney, Agent, or Firm*—Frishauf, Holtz, Goodman & Woodward

[57] ABSTRACT

The invention provides a process for producing coenzyme $Q_{10}$ by cultivating a novel microorganism JY-155 which belongs to the genus Trichosporon (FERM-P4650, ATCC 20566) which we discovered, in a culture medium containing sulfite waste liquor as the carbon source. The microbial cells form and accumulate coenzyme $Q_{10}$. These cells are then recovered from the culture and processed to obtain the coenzyme $Q_{10}$ as a compound or to obtain it in usable form while still associated with at least some of the cell material.

8 Claims, No Drawings

PROCESS FOR PRODUCING COENZYME $Q_{10}$

BACKGROUND OF THE INVENTION

The present invention provides a method for producing coenzyme $Q_{10}$.

Coenzyme $Q_{10}$ plays an important function as an element of the electron transmission system in an organism. It is known to exhibit an excellent pharmaceutical effect against various diseases. In recent years, it has been clinically employed for curing of cardiac insufficiency by oral administration.

Coenzyme $Q_{10}$ has the formula

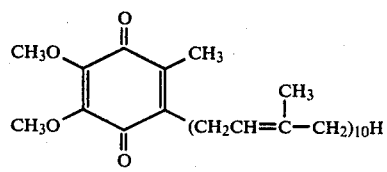

Coenzyme $Q_{10}$ is industrially produced either by a semisynthetic process that uses a material originating in plants, or by a fermentation process that extracts said compound from microbial cells. In the fermentation process, it is necessary to produce microbial cells containing coenzyme $Q_{10}$ at a low cost in order to realize an industrially feasible process because the amount of coenzyme $Q_{10}$ accumulated in the individual microbial cells is small.

Methods of extracting coenzyme $Q_{10}$ from microorganisms, especially from yeast and the like, are disclosed in Japanese Patent Publication No. 8836/1973, Japanese Patent Publication No. 19034/1976 and Japanese Patent Laid-open Publication No. 105288/1977. A process for producing coenzyme $Q_{10}$ characterized by the use of higher fatty acid as a substrate in the cultivation of yeast is disclosed in Japanese Patent Publication No. 4758/1975 is known.

In processes utilizing microbial cells, it is usually of importance that the component of the culture medium serving as a primary source of carbon for the growing microbial cells be an inexpensive material. It is an object of the present invention to provide an economic fermentation process for producing coenzyme $Q_{10}$, and particularly such a process using an inexpensive carbon source as a component of the culture medium.

The process of producing sulfite pulp from wood produces a waste liquor from the cooking of wood referred to industrially and hereinafter as SWL. SWL has been employed in the production of yeast of the type used as a food and also as a feed component for animals. Recently SWL has been used as a source material for the production of a particular yeast belonging to the genus Torula from which useful (active) components such as nucleic acid and glutathione are extracted. SWL contains saccharoid, acetic acid and alcohols that are useful for the cultivation of yeast. However, SWL also contains many substances, such as sulfurous acid, decomposition products of lignin, furfural, formic acid and loosely combined sulfite, which inhibit the growth of yeasts. As a consequence, SWL is generally a substance having a poor capability as a culture medium for yeasts in general. The specific types of yeast which can grow in a culture medium containing SWL as a main carbon source are limited. Only the aforesaid genus Torula and the like are cultivated in an SWL-containing medium on an industrial scale.

Because of the inexpensive nature of SWL, we have endeavored to provide a process for producing coenzyme $Q_{10}$ from a microorganism which can assimilate SWL.

THE INVENTION

The present invention provides a process for producing coenzyme $Q_{10}$, which comprises cultivating the microorganism JY-155 which belongs to the genus Trichosporon (FERM-P4650, ATCC 20566) in a culture medium containing sulfite waste liquor (SWL) as the carbon source until said coenzyme $Q_{10}$ is formed and accumulated in a substantial amount in the culture, and recovering said coenzyme $Q_{10}$ therefrom. The said sulfite waste liquor preferably is a sulfite waste liquor which contains from 0.5 to 4 percent by weight of sugar in terms of glucoside content. The culture medium preferably also contains a nitrogen source and inorganic salt together with said sulfite waste liquor.

The microorganism employed in this process is the strain JY-155 which belongs to the genus Trichosporon which we separated from the soil and discovered. This strain can grow vigorously in a culture medium containing SWL as the main carbon source and accumulates coenzyme $Q_{10}$ in its cells. In addition to the Trichosporon JY-155 which we have discovered, it is also possible to use Trichosporon JY-155 which is modified by various means of artificial modification when such modified Trichosporon JY-155 is capable of producing coenzyme $Q_{10}$ when grown in a culture medium containing SWL.

In the process of the present invention SWL is used as it is or after being diluted to a sugar concentration of from 0.5 to 4% (calculated as glucose). A culture medium can be employed which contains an assimilable nitrogen source, other inorganic salts and growth promoters, such as vitamins, as well as SWL. Such nitrogen sources include aqueous ammonia, ammonium salts (ammonium sulfate, ammonium phosphate, etc.), urea, peptone, meat extract, and other inorganic or organic nitrogen containing substances. Other illustrative inorganic salts include phosphate, magnesium salt, calcium salt, iron salt, manganese salt, sodium chloride, potassium chloride and, if desirable, salts of trace metals. Growth promoters include vitamins, amino acids, yeast extract, corn steep liquor, etc.

Cultivation is performed by shaking aerobically or stirring with air feeding. The cultivation temperature is preferably in the range of from 25° to 37° C. The pH value for cultivation is maintained in the range of from 4 to 8. The type of cultivation may be of either the batch type (10 hours to 5 days in cultivation period) or the continuous type. The latter is preferable for cultivation on an industrial scale.

Microbial cells are separated from the culture broth by methods such as centrifugating, filtration, etc. The separated cells contain coenzyme $Q_{10}$ which has accumulated thereon. After being dried and optionally additionally processed, they can be used as nutrients, medicine and other applications.

The cells from which coenzyme $Q_{10}$ is separated may be living cells, dry cells or treated cells. Separation of coenzyme $Q_{10}$ from the cells can be done by conventional methods. For example, to extract coenzyme $Q_{10}$, the saponifiable substance contained in the cells is saponified by using methanol alkali or ethanol alkali in the presence of pyrogallol. Coenzyme $Q_{10}$ from thus saponified liquid is dissolved in a solvent such as n-hexane or petroleum ether. Thereafter, fractional refining is performed by using alumina, silica gel, florizil or the like, and recrystallization is then repeated to obtain pure crystals of coenzyme $Q_{10}$.

The Trichosporon strain JY-155 which we have discovered has the following microbiological properties.

(a) Growth in culture medium (1) Malt extract medium (liquid)

Budding is polipolar. A film is formed. The form is an elongated ellipsoid of 2.2 to 6.5 micron by 6.7 to 16.2 micron.

(2) MY agar medium

Growth is vigorous. Fringe of colony is wavelike. Elevation of colony is coniform or convex. There is a hollow at the center of colony. Surface of colony is rough and luster of colony is chalky. Property of colony is tough.

(3) Slide culture on potato extract agar medium

Mycelium and pseudomycelium are formed, and bud spore and oidium are formed.

(4) Slide culture on MY agar medium

Endospore is formed.

(b) Formation of Ascospore

Ascospore is not formed.

(c) Formation of projective spore

Projective spore is not formed.

(d) Physiological properties (1) Optimum condition
  pH: 5 to 7
  Temperature: 27° to 35° C.

(2) Growing range
  pH: 3 to 11.5
  Temperature: 15° to 45° C.

(3) Assimilation of nitrate: No
(4) Decomposition of fat: No
(5) Decomposition of urea: Yes
(6) Liquefaction of gelatin: No
(7) Tolerance to osmotic pressure with salt: The strain can grow at a salt concentration up to 12%.
(8) Formation of amyloidal substance: No
(9) Formation of organic acid: No
(10) Formation of carotinoid: No
(11) Requirement of vitamin: Thiamine is required
(12) Decomposition of arbutin: No
(13) Formation of ester: No
(14) Reactivity of litmus milk: No
(15) Cycloheximide tolerance: Yes
(16) Extinction temperature: 50° C.

(e) Fermentation of saccharoid: No (f) Assimilation of carbon source

| | | | |
|---|---|---|---|
| D-glucose | + | D-glucitol | + |
| D-galactose | + | α-methyl-D-glucoside | + |
| L-sorbose | + | Salicin | + |
| Sucrose | + | Arbutin | + |
| Maltose | + | DL-lactate | + |
| Cellobiose | + | Citrate | + |
| Trehalose | + | Succinate | - |
| Lactose | + | Inositol | - |
| Melibiose | + | D-mannose | + |
| Raffinose | + | D-fructose | + |
| Melezitose | + | Potassium gluconate | - |
| Inulin | | Calcium salt of α-ketogluconic acid | + |
| Soluble starch | + | | |
| D-xylose | + | Acetate | + |
| L-arabinose | + | Dextrin | + |
| D-arabinose | - | | |

-continued

| | |
|---|---|
| D-ribose | + |
| L-rhamnose | + |
| Ethanol | + |
| Glycerin | + |
| Erythritol | + |
| Adonitol | + |
| Garactitol | + |
| D-mannitol | + |

When the above-described properties are examined in comparison with those described in "The Yeast. A Taxonomic Study" (1970) by J. Lodder et al., this strain is considered to belong to genus Trichosporon. In this genus, however, there is no prior species which is identical with this JY-155 strain. For example, this strain is similar to *Trichosporon cutaneum*, a known strain, but is found clearly different from this known strain in regard to assimilation of inositol and also in regard to sulfite tolerence, furfural tolerance and assimilation of SWL as shown in the following Tables 1 and 2.

Therefore, we consider this strain to be a new species and have named it Trichosporon JY-155. This strain has been given the name FERM-P4650 and ATCC 20566 and was deposited in Fermentation Research Institute, Agency of Industrial Science and Technology, Japan and American Type Culture Collection, Rockville, Maryland, U.S.A., respectively.

TABLE 1*

| Strain | Growth when sulfite is added | Growth when loosely combined sulfite is added | Growth when furfural is added |
|---|---|---|---|
| Trichosporon JY-155, ATCC 20566 | Yes | Yes | Yes |
| Trichosporon cutaneum IFO-173 | No | No | No |
| Trichosporon cutaneum IFO-598 | No | No | No |
| Trichosporon cutaneum IFO-1200 | No | No | No |
| Trichosporon cutaneum IFO-1489 | No | No | No |

*Test Method

The test was done according to the test method for assimilation of carbon source, one of the microbiological properties. To a culture medium containing 1% of glucose as carbon source was added 0.5% (W/V) of $Na_2SO_3$ as sulfite or 2% (V/V) of a mixture solution of 1 mole of sodium bisulfite as loosely combined sulfite and 0.3 mole of formaldehyde and 0.3 mole of acetaldehyde or 0.1% (W/V) of furfural. Turbidity was examined with the naked eye to see whether or not the strain had grown.

TABLE 2*

| | Assimilation of SWL | |
|---|---|---|
| Strain | Sugar consumption (%) | Concentration of formed cells (g/l) |
| Trichosporon JY-155 ATCC 20566 | 77.3 | 9.7 |
| Trichosporon cutaneum IFO-173 | 4.2 | 0.6 |
| Trichosporon cutaneum IFO-598 | 6.3 | 0.7 |
| Trichosporon cutaneum IFO-1200 | 2.1 | 0.3 |
| Trichosporon cutaneum IFO-1489 | 5.0 | 0.9 |

*Test Method

Into a 500 milliliters Sakaguchi's flask was put 50 milliliters of a culture medium comprising 1% of glucose, 0.15% of urea, 0.15% of $KH_2PO_4$, 0.02% of $MgSO_4.7H_2O$, 0.01% of $CaCl_2.2H_2O$, 0.01% of NaCl and 0.02% of powdered yeast extract. The culture medium was inoculated with each of the above strains, and preliminary cultivation was performed with shaking at 30° C. for 24 hours. Thereafter, SWL was diluted to obtain an initial sugar concentration of 1.4%. To thus diluted SWL was added a substance having the same composition as the preliminary culture medium with the exception of glucose, thereby a culture medium containing SWL was prepared. To this culture medium was added 5 milliliters of the preliminary culture broth, and cultivation was performed in the same condition as the preliminary cultivation.

The invention is further illustrated by the following example.

EXAMPLE

A 500 milliliters Sakaguchi's flask containing 50 milliliters of a culture medium comprising 1% of glucose, 0.15% of urea, 0.15% of $KH_2PO_4$, 0.02% of $MgSO_4.7H_2O$, 0.01% of $CaCl_2.2H_2O$, 0.01% of NaCl and 0.2% of powdered yeast extract (pH 5.5) was inoculated with Trichosporon JY-155 (FERM-P4650, ATCC 20566). Preliminary cultivation was performed with shaking at 30° C. for 24 hours, and the thus obtained culture broth was placed in a culture medium in a 30 liters fermentation tank in an amount of 5%. SWL was diluted to adjust to a sugar concentration of 10 grams per liter, and the initial composition of the SWL medium for batch cultivation was made up by adding 0.15% of ammonium sulfate, 0.15% of $KH_2PO_4$, 0.02% of $MgSO_4.7H_2O$, 0.01% of NaCl and 0.05% of powdered yeast extract. Cultivation was performed under the following conditions: The cultivation temperature was 32° C.; the air feed rate was 18 liters per minute; and the rotational speed was 410 rounds per minute; the quantity of liquid medium in tank was 18 liters; and the pH value was 5.1. When the growth of the yeast entered into the logarithmic phase, continuous cultivation was started and carried out by feeding the SWL medium continuously. The stock SWL medium had the same contents of inorganic salts as the medium for batch cultivation, had a sugar concentration of 30 grams per liter in SWL and 2 ppm of thiamine-hydrochloride were added thereto instead of powdered yeast extract. Cultivation was controlled by maintaining 70% sugar consumption, and a steady state was reached. At that time, the yeast concentration in the rank was around 1.3%. By centrifuging 30 liters of overflowed broth from a fermentation tank, 1820 grams of wet cells were obtained (corresponds to 337 grams of dry cells; said cells contained 840 milligrams of coenzyme $Q_{10}$ per 1 gram of dry cells). These cells were mixed with 3.6 liters of methanol, 180 grams of pyrogallol and 900 milliliters of 60% caustic potash, and the mixture was refluxed with heating at 80° C. for one hour. After the mixture was cooled, the coenzyme $Q_{10}$ containing fraction was extracted twice by 3 liters of n-hexane and was dissolved in a layer of n-hexane. This n-hexane in which the coenzyme $Q_{10}$ containing fraction was dissolved was washed with water until it became neutral, and then dried with Glauber's salt followed by concentration and evaporation. The residue was dissolved in acetone; the acetone removed by evaporation; and the residue dissolved in n-hexane. This solution was developed into silica gel column using a mixture of ether and n-hexane, and the eluate containing coenzyme $Q_{10}$ was collected through fractionation. The solvent in this eluate was removed therefrom by evaporation. The residue was dissolved in a small amount of ethanol and allowed to stand in a cold place to precipitate crude crystals of coenzyme $Q_{10}$. By repeating recrystallization from ethanol (three times), 106 milligrams of crystals of coenzyme $Q_{10}$ were obtained. This compound exhibited a melting point of from 48° to 50° C. and was confirmed to be coenzyme $Q_{10}$ from the tests of thin-layer chromatography, liquid chromatography, UV absorption spectrum and mass spectrum.

We claim:

1. A process for producing coenzyme $Q_{10}$ comprising cultivating the microorganism JY-155 which belongs to the genus Trichosporon (FERM-P4650, ATCC 20566) in a culture medium containing sulfite waste liquid as the carbon source to form and accumulate substantial amounts of coenzyme $Q_{10}$ in the culture, and then separating cultivated culture containing said coenzyme $Q_{10}$ from said culture to recover coenzyme $Q_{10}$ containing material.

2. The process of claim 1 wherein the sulfite waste liquor contains between 0.5 and 4% by weight of sugar in terms of glucoside content.

3. The process of claim 1 wherein said culture medium also contains a source of nitrogen and at least one inorganic salt.

4. The process of claim 2 wherein said culture medium also contains a source of nitrogen and at least one inorganic salt.

5. The process of claim 1 or claim 2 wherein said cultivation is carried out at a temperature between about 25° to 37° C.

6. The process of claim 4 wherein said cultivation is carried out at a temperature between about 25° and 37° C.

7. The process of claim 1 or claim 2 or claim 3 or claim 6 wherein said culture medium has a pH from about 4 to 8.

8. The process of claim 5 wherein said culture medium has a pH from about 4 to 8.

* * * * *